United States Patent
Mahmoud et al.

(10) Patent No.: US 10,576,119 B2
(45) Date of Patent: Mar. 3, 2020

(54) SOUR CHERRY TOPICAL THERAPEUTIC FORMULATIONS, METHOD OF MANUFACTURE AND METHOD OF TREATMENT OF HUMAN OSTEOARTHRITIS SYMPTOMS

(71) Applicants: Fadia F. Mahmoud, Sulaibikhat (KW); David D. Haines, Debrecen (HU)

(72) Inventors: Fadia F. Mahmoud, Sulaibikhat (KW); David D. Haines, Debrecen (HU)

( * ) Notice: Subject to any disclaimer, the term of this patent is extended or adjusted under 35 U.S.C. 154(b) by 146 days.

(21) Appl. No.: 15/923,253

(22) Filed: Mar. 16, 2018

(65) Prior Publication Data

US 2018/0207220 A1   Jul. 26, 2018

Related U.S. Application Data

(62) Division of application No. 14/874,065, filed on Oct. 2, 2015.

(60) Provisional application No. 62/059,232, filed on Oct. 3, 2014.

(51) Int. Cl.
| | |
|---|---|
| *A61K 36/736* | (2006.01) |
| *A61K 9/00* | (2006.01) |
| *A61K 45/06* | (2006.01) |
| *A61K 9/107* | (2006.01) |
| *A61K 9/06* | (2006.01) |

(52) U.S. Cl.
CPC .......... *A61K 36/736* (2013.01); *A61K 9/0014* (2013.01); *A61K 9/06* (2013.01); *A61K 9/107* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 4,661,343 | A | * | 4/1987 | Zabotto .................. A61K 8/922 424/59 |
| 2009/0238903 | A1 | * | 9/2009 | Tosaki ................. A61K 31/353 424/735 |
| 2010/0008886 | A1 | * | 1/2010 | Tosaki ................... A61K 8/922 424/74 |

FOREIGN PATENT DOCUMENTS

JP     2006176414 A  *  7/2006

OTHER PUBLICATIONS

Bak et al. Phytother. Res. 25: 1714-1720. (Year: 2011).*
Science Daily. "Tart Cherries May Reduce Factors Associated With Heart Disease and Diabetes". Internet publication date: Apr. 12, 2008 [retrieved from the Internet on: Mar. 23, 2019]. Retrieved from: <URL: https://www.sciencedaily.com/releases/2008/04/080407114647.htm>. (Year: 2008).*
Schaefer, K. "Cherry Seed Oil for Hydration and Antioxidation" from Cosmetics & Toiletries. Apr. 20, 2012. Retrieved from the Internet : <URL: https://www.cosmeticsandtoiletries.com/formulating/function/moisturizer/148272915.html>. (Year: 2012).*
Frangogiannis et al. Cardiovascular Research 53. 31-47. (Year: 2002).*

* cited by examiner

*Primary Examiner* — Amy L Clark
(74) *Attorney, Agent, or Firm* — Thomas C. Saitta (57) ABSTRACT

A biotherapeutic anti-inflammatory composition, its method of manufacture and method of treatment of various diseases, the composition having an efficacious amount of solid sour cherry seed extract and sour cherry seed oil sufficient to inhibit production of disease-associated inflammatory cytokines by CD3+ T lymphocytes in a vertebrate mammal.

12 Claims, 6 Drawing Sheets

SOUR CHERRY TOPICAL THERAPEUTIC FORMULATIONS, METHOD OF MANUFACTURE AND METHOD OF TREATMENT OF HUMAN OSTEOARTHRITIS SYMPTOMS

This application claims the benefit of U.S. Provisional Patent Application Ser. No. 62/059,232, filed Oct. 3, 2014, and is a divisional application of pending U.S. patent application Ser. No. 14/874,065, filed Oct. 2, 2015.

BACKGROUND OF THE INVENTION

This invention relates in a general sense to topical biotherapeutic formulations, methods of manufacture of such formulations, and methods of treatment of human osteoarthritis and other inflammatory diseases. In a more particular sense, the invention relates to such formulations and methods that utilize compositions extracted from sour cherry seeds.

Osteoarthritis (OA) treatments presently rely on analgesics, which manage pain but fail to restore imbalances between catabolic and anabolic processes underlying OA pathogenesis. Previously developed biotherapeutic drugs (also known as biologics or biopharmaceuticals), which alter the activity of catabolic agents such as nitric oxide and inflammatory cytokines and allow tissue regeneration, were evaluated for efficacy in OA treatment. These studies failed to demonstrate dramatic abatement of OA symptoms by such drugs.

Osteoarthritis (OA), a degenerative age-related disease that affects the joints, is the most common human musculoskeletal disorder, and a leading cause of disability in elderly populations worldwide. OA onset is typically triggered by sustained biomechanical trauma, resulting in chondrocyte-mediated cartilage destruction.

Oxidative stress, created by this degradative process, promotes emergence of senescent osteoarthritic osteoblasts, which in turn enhance dysregulation of pro-inflammatory signaling and apoptotic depletion of functional joint cells, causing insufficient cartilage repair and aberrant remodeling of the extracellular matrix. Tissue damage is exacerbated by trauma-related dysregulation of normal maintenance of healthy joint homeostasis. This disruption promotes increasingly severe inflammation (synovitis), leading to adverse changes in joint fluid composition, breakdown of extracellular matrix material, and impairment of normal tissue repair.

The pathomechanisms of OA are facilitated by progressively elevated levels of the inflammatory cytokines TNF-α, and the interleukins (IL) IL-1β, IL-6, and IL-8, produced primarily by macrophages and T lymphocytes, systemically and in affected joint tissue. Signaling cascades downstream of these cytokines also increases expression of nitric oxide (NO) by mesenchymal cells (Volpi and Maccari 2005). Collectively, each of these factors contribute to joint capsule thickening, along with loss of cartilage, chondrocyte apoptosis, progressive articular dysfunction, and extreme chronic pain.

Figure 1:
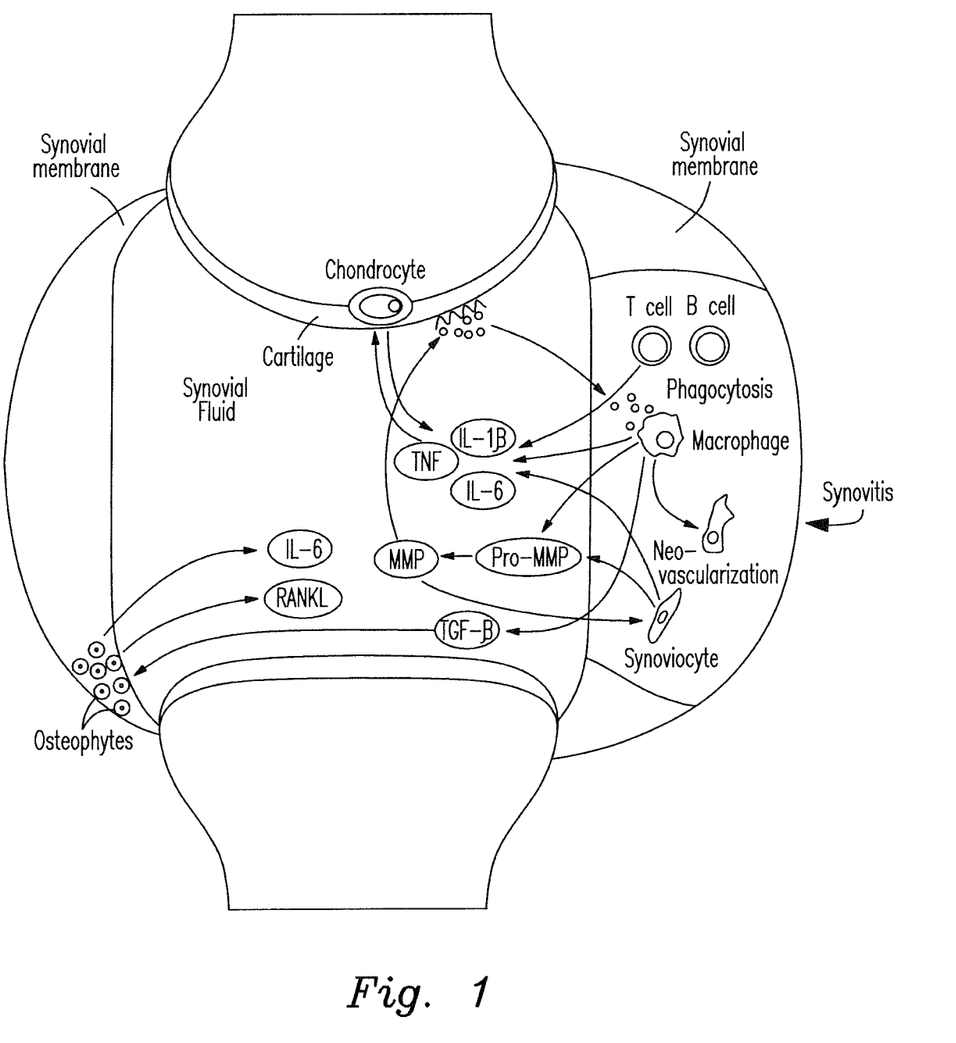
FIG. 1 is an illustration of major pathomechanisms contributing to OA-associated articular tissue damage in a human joint. Mechanical trauma and endogenous oxidative stressors increase synoviocyte, T cell, and macrophage expression of the inflammatory cytokines TNF-α, and IL-6, resulting in aberrant chondrocyte activity and damaged cartilage. Increased macrophage TGF-β expression stimulates bone tissue osteophytes, promoting joint inflammation. Pathologically elevated macrophage activity also increases neovascularization, increasing production of pro-matrix metaloproteinase (ProMMP), which activates its collagenase function by autocatalytic cleavage, allowing it to contribute to OA-associated collagen matrix destruction.

Several well-known features of the OA disease process that present very attractive therapeutic targets are illustrated in FIG. 1. For example, the production of inflammatory cytokines by activated CD3+T lymphocytes offers an excellent "choke point" for intervention in OA pathogenesis. This is due to critical roles for these mediators in disease-associated pain and articular tissue destruction. Many treatments interfere with inflammatory cytokines at the level of their interaction with their normal physiological receptors and block downstream signaling processes, including dysregulated inflammation. However, a class of agents known as biotherapeutic drugs is distinguished by mechanisms that modulate cellular signaling pathways to interfere with disease progression, promoting activities that contribute to healthy homeostasis. These approaches differ from use of analgesics and related drugs currently favored in clinical practice, which may ameliorate pain and other symptoms, but have a negligible effect on the fundamental pathomechanisms of OA.

Previous clinical trials of inflammatory cytokine inhibitors reported by other investigators failed to produce dramatic improvement of OA prognoses. Inhibitors of both TNF and IL-1β were constructed as fusion products of a synthetic genetic element containing a portion of the gene for cognate receptors of TNF or IL-1β, spliced to the Fc (constant) portion of the Immunoglobin G1 (IgG1) antibody. The resulting fusion protein binds to each cytokine, competitively reducing their physiological availability, thereby inhibiting their pro-inflammatory effects. In OA, this includes destruction of joint tissue (FIG. 1). These agents, administered systemically or via intra-articular injection to OA patients affected in both knees and hands, failed to halt structural deterioration or severity of symptoms. Moreover, genetically engineered cytokine inhibitors are extremely costly. For instance, per-patient costs for a one-year regimen of Etanercept, a TNF-inhibitory fusion protein with broad application in inflammatory disease, is approximately $20,000. This class of drug and related products is also associated with severe side effects, including cancer and, occasionally, fatal immune impairment.

The lack of effective biopharmaceutical strategies for OA management has left clinicians heavily dependent on corticosteroids and non-steroidal anti-inflammatories. Despite being highly effective in controlling inflammation, these drugs are often severely toxic, particularly over extended time periods. Conversely, biotherapeutic strategies avoid small molecule inhibitors of pro-inflammatory signaling cascades—which may be costly, toxic, and only marginally effective.

It is an object of this invention to provide a novel formulation or composition of matter comprising the combination of sour cherry seed extract (SCE) and sour cherry seed oil (SCO) as an inducer of heme oxygenase-1 (HO-1), a major physiological protectant against oxidative stress, in order to significantly reduce joint pain and activation of CD4+ T cells expressing inflammatory cytokines ($p<0.05$); to significantly decrease peripheral blood c-reactive protein (CRP); and to significantly increase leukocyte HO-1 ($p<0.05$). The composition inhibits joint-damaging inflammatory mediator production, thereby meeting the main criterion for classification as a biotherapeutic, i.e., an agent that inhibits disease pathogenesis rather than merely managing pain or reducing symptoms. It is a further object to provide a method of manufacture whereby the composition is formulated as a topical cream, and a further object to provide a method of treatment by topical application of the composition wherein systemic concentrations of bioactive compounds are delivered transdermally to ameliorate inflammation.

SUMMARY OF THE INVENTION

In one aspect or embodiment, the invention is a topical cream composition comprising a stable mixture of sour cherry seed extract (SCE) and sour cherry seed oil (SCO), an emulsion comprising the solid, flavonoid-rich fraction of sour cherry (Prunus cerasus) seed suspended in the oil fraction of the sour cherry seed. The solid, flavonoid-rich fraction (SCE) and the oil fraction (SCO) are obtainable as separate components by methods known in the art. A novel method of manufacture is required to produce the topical composition as an even and phase-stable suspension in oil of multiple compounds of differential solubility. This composition contains natural excipients, such as oleic acid, which facilitate transdermal migration of bioactive compounds, resulting in systemic concentrations of these compounds high enough to cause the desired physiologic effects.

In another aspect of embodiment, the invention is a method of systemically controlling inflammatory signaling in vertebrate animals (mammals and humans) to levels that prevent or mitigate tissue damage in all disease states in which symptoms result from dysregulated inflammation, using a topically-applied biotherapeutic composition of sour cherry seed kernel emulsion comprising a mixture of the flavonoid-rich solid fraction of the seed (SCE) and the oil of the seed (SCO).

In another aspect or embodiment, the invention is a method in which a phase-stable emulsion is manufactured that disperses the bioactive components of the solid fraction of sour cherry (Prunus cerasus) seed kernel (SCE) in an oil phase, which comprises sour cherry seed oil (SCO) and other selected oils suitable for human cosmetic use. Briefly, a lipophilic component and a separate hydrophilic component are prepared, melted separately and then combined in the melted state to create a cream base. After the cream base has cooled, the SCE and SCO active ingredients are added and mixed in.

DETAILED DESCRIPTION

In general, the composition of the invention is a topically applied, biotherapeutic blend of phytochemicals that interferes with OA pathogenesis by reducing the number of T lymphocytes activated to produce disease-associated inflammatory cytokines. The combination of sour cherry seed extract (SCE) and sour cherry seed oil (SCO) systemically increases the activity of HO-1, a major naturally-occurring antioxidant defense enzyme, ameliorates OA symptoms, and inhibits activation of CD3+ T cells to express inflammatory cytokines. HO-1 does not directly inactivate reactive oxygen molecules. Rather, its contribution to antioxidant defense occurs indirectly due to two major heme degradation products of HO-1 activity: bilirubin and carbon monoxide (CO). The enzyme metabolizes heme that accumulates in tissues as a result red blood cell turnover to CO, free iron and bilverdin. Biliverdin is rapidly reacted to bilirubin by ubiquitously expressed biliverdin reductase, and in nanomolar intracellular concentrations acts as a powerful scavenger of reactive oxygen molecules. CO exerts its cytoprotective effects through increases in the activity of guanylate cyclase to increase levels of the second messenger cyclic guanosine-3'5'-monophosphate (cGMP), which interact with multiple cellular targets to reduce oxidative stress. SCE/SCO-induced HO-1 inhibits the representation of CD3+TNF-α+ and CD3+IL-8+ cells in cultured leukocytes from human rheumatoid arthritis and diabetes type 2 patients at significantly greater levels than in cells from healthy control subjects. These findings are highly encouraging, as both rheumatoid arthritis and type 2 diabetes are chronic inflammatory diseases with many features of pathogenesis—particularly inflammatory tissue destruction—in common with OA.

The terms "biotherapetic", biologic" or "biopharmaceutical" define an agent that alters the fundamental underlying cause of a disease, rather than simply treating symptoms on a temporary basis. This definition is given to the terms as used herein.

The topically administered SCE/SCO composition described herein is considered a biotherapeutic because it directly inhibits the activity of inflammatory cytokines, which are core contributors to the disease. Components of the SCE/SCO composition curtail cytokine expression by T cells via increased tissue activity of HO-1. Studies suggest that phytochemical inducers of this enzyme are potentially superior to fusion protein biopharmaceuticals, which inhibit cytokine activity at the level of interaction with their cognate receptors.

The invention relates to control of inflammation that has become dysregulated in ways that result in tissue damage characteristic of a wide variety of diseases. The invention is a topical preparation in emulsion form of phytochemicals which penetrate the skin and become systemically bioavailable in efficacious concentration to significantly inhibit primary immune activation that is responsible for inflammatory disease symptoms. Diseases which exhibit features that this invention has been shown to therapeutically affect, include, but are not limited to the following representative disorders: Osteoarthritis, Rheumatoid Arthritis, Allergic Rhinitis, Multiple Sclerosis, Uveitis, Autoimmune Diabetes (type I, IDDM), Type 2 Diabetes (metabolic syndrome), Bronchial Asthma, Psoriasis Vulgaris, Eczema, Systemic Lupus Erythematosus (SLE), Alopecia Aereata, Hashimoto's Thyroiditis, IgA Nephropathy, Hydrops, Kell Erythroblastosis Fetalis and Pemphigus.

All diseases that include underlying pathomechanisms caused by dysregulated inflammatory processes exhibit common features that may be exploited in strategies for prevention and therapy. It has been shown that the SCE/SCO composition described herein affects activation of CD3+ T cells in ways that significantly ameliorated joint pain and disease-associated biomarkers in human OA patients. Osteoarthritis was selected as a model disease for demonstration of this invention since it has core pathomechanisms in common with a wide range of disorders, but the invention is applicable to other inflammation-inducing diseases as well.

OA is a degenerative age-related disease that affects the joints, is the most common human musculoskeletal disorder, and is a leading cause of disability in elderly populations worldwide. OA onset is typically triggered by sustained biomechanical trauma, resulting in chondrocyte-mediated cartilage destruction. Oxidative stress, created by this degradative process, promotes emergence of senescent osteoarthritic osteoblasts, which in turn enhance dysregulation of pro-inflammatory signaling and apoptotic depletion of functional joint cells, causing insufficient cartilage repair and aberrant remodeling of the extracellular matrix. Tissue damage is exacerbated by trauma-related dysregulation of normal maintenance of healthy joint homeostasis. This disruption promotes increasingly severe inflammation (synovitis), leading to adverse changes in joint fluid composition, breakdown of extracellular matrix material, and impairment of normal tissue repair. The pathomechanisms of OA are facilitated by progressively elevated levels of the inflammatory cytokines TNF-α, and the interleukins (IL) IL-1β, IL-6, and IL-8, produced primarily by macrophages and T lymphocytes, systemically and in affected joint tissue. Signaling cascades downstream of these cytokines also increases expression of nitric oxide (NO) by mesenchymal cells. Collectively, each of these factors contribute to joint capsule thickening, along with loss of cartilage, chondrocyte apoptosis, progressive articular dysfunction, and extreme chronic pain.

In one aspect or embodiment, the invention is a topical cream composition comprising sour cherry seed extract (SCE) and sour cherry seed oil (SCO), presented as an emulsion comprising the solid, flavonoid-rich fraction of sour cherry (*Prunus cerasus*) seed suspended in the oil fraction of the sour cherry seed. The solid, flavonoid-rich fraction (SCE) and the oil fraction (SCO) are obtainable as separate components for subsequent mixing by methods known in the art. In particular, methodology for obtaining SCE and SCO is set forth in Bak I et al. (2010) "Isolation and analysis of bioactive constituents of sour cherry (*Prunus cerasus*) seed kernel; an emerging functional food." *J. Med Food* 13:905-910, the disclosure of which is incorporated herein by reference.

A novel method of manufacture is required to produce the SCE/SCO composition as an even and phase-stable suspension in oil of multiple compounds of differential solubility, as prior efforts have resulted in undesirable precipitation. This composition contains natural excipients, such as oleic acid, which facilitate transdermal migration of bioactive compounds, resulting in systemic concentrations of these compounds high enough to cause the desired physiologic effects.

In another aspect of embodiment, the invention is a method of systemically controlling inflammatory signaling in vertebrate animals to levels that prevent or mitigate tissue damage in all disease states in which symptoms result from dysregulated inflammation, using a topically-applied biotherapeutic composition comprising a mixture of the solid (i.e., powder form) flavonoid-rich solid fraction of the seed (SCE), the oil fraction of the seed (SCO) and other selected compounds.

In another aspect or embodiment, the invention is a method in which a phase-stable emulsion is manufactured that disperses the bioactive components SCE and SCO of the sour cherry (*Prunus cerasus*) seed. The process for extracting the kernel contents of sour cherry seeds, separation of the oil fractions and preparation of the powdered extract used to prepare the topical product is known in the art.

The method of manufacture comprises the steps of:
(a) creating a lipophilic component comprising a mixture of various ingredients;
(b) creating a hydrophilic component comprising a mixture of various ingredients;
(c) heating the lipophilic components and the hydrophilic components separately until all the ingredients are melted or liquified and both components are at approximately the same temperature;
(d) combining and mixing both components while at the same temperature and with all the components in the melted or liquified state and allowing the mixed components to cool to ambient temperature to form a cream base;
(e) adding the sour cherry seed oil (SCO) into the cream base and mixing;
(f) adding sour cherry seed extract SCE) in powdered form into the cream base and mixing.

In a preferred embodiment, the two components are heated separately in a water bath at a temperature of approximately 50-60° C. The SCE/SCO topical composition should be stored in a dark, cool place at approximately 2-8° C. Preferably the solid sour cherry seed extract (SCE) and the solid cherry seed oil (SCO) are each present in the SCE/SCO composition at approximately 3-5 wt %.

Prior attempts at mixing the solid, flavonoid-rich fraction (SCE) and the oil fraction (SCO) have not been successful in producing a highly stable mixture. The methodology set forth above, however, produces a highly stable emulsion composition with evenly blended sour cherry seed lipid soluble components and water soluble components. The SCE/SCO composition so produced is a highly efficient and effective biotherapeutic, anti-inflammatory, topical cream base composition.

A representative and efficacious biotherapeutic SCE/SCO composition may comprise the following ingredients, presented by weight percent and with illustrative weights for production of a 5000 gram (g) batch of the composition, the weight percentages and weights being approximate:

| Wt Percent | Weight | |
|---|---|---|
| 5 wt % | 250 g | lanolin (a.k.a wool fat) |
| 5 wt % | 250 g | cetylic and stearylic alcohol |
| 10 wt % | 500 g | stearin |
| 5 wt % | 250 g | isopropyl myristate |
| 0.8 wt % | 40 g | vitamin C |
| 2 wt % | 100 g | sodium lauryl sulphate |
| 5 wt % | 250 g | glycerin |
| 5 wt % | 250 g | propylene glycol |
| 52.2 wt % | 2610 g | distilled water |
| 5 wt % | 250 g | sour cherry seed oil (SCO) |
| 5 wt % | 250 g | powdered sour cherry seed extract (SCE) |

The lipophilic component in this example consists of the mixture of lanolin, cetylic and stearylic alcohol, stearin and isopropyl myristate. Based on the weight percentages above, the lipophilic component comprises approximately 20 wt % lanolin, approximately 20 wt % cetylic and stearylic acid, approximately 40 wt % stearin and approximately 20 wt % isopropyl myristate. The hydrophilic component in this example consists of the mixture of vitamin C, sodium lauryl sulphate, glycerin, propylene glycol and distilled water. The hydrophilic component comprises approximately 1.2 wt % vitamin C, approximately 3.1 wt % sodium lauryl sulphate, approximately 7.7 wt % glycerin, approximately 7.7 wt % propylene glycol, and approximately 80.3 wt % water.

The SCE/SCO composition as described has been found to provide the following when topically applied to vertebrate mammals, including humans:

(a) Significant suppression ($p<0.05$) of osteoarthritis-associated joint pain.

(b) Significant inhibition ($p<0.05$) of the inflammation-associated serum biomarker of inflammation, c-reactive protein (CRP).

(c) Significant increased ($p<0.05$) expression of heme oxygenase-1 (HO-1) by peripheral blood leukocytes to therapeutic levels.

(d) Significant inhibition ($p<0.05$) of production of disease-associated inflammatory cytokines by CD3+T lymphocytes at levels capable of ameliorating symptoms of osteoarthritis.

The method of treatment comprises the steps of applying the SCE/SCO composition as described and manufactured above topically to the skin of a vertebrate mammal in repeated applications such that the SCE and SCO ingredients migrate into and through the skin to an area of inflammation.

The SCE/SCO composition addresses the type of inflammation associated with Osteoarthritis, Rheumatoid Arthritis, Allergic Rhinitis, Multiple Sclerosis, Uveitis, Autoimmune Diabetes (type I, IDDM), Type 2 Diabetes (metabolic syndrome), Bronchial Asthma, Psoriasis Vulgaris, Eczema, Systemic Lupus Erythematosus (SLE), Alopecia Aereata, Hashimoto's Thyroiditis, IgA Nephropathy, Hydrops, Kell Erythroblastosis Fetalis and Pemphigus.

The beneficial and efficacious results of the topical application of the SCE/SCO composition as described herein has been demonstrated in a representative clinical trial directed to the treatment of osteoarthritis (OA):

Study Participants

Participants included 30 patients aged 40 years or older, diagnosed with inflammatory OA of the knee, according to criteria for OA set by the American College of Rheumatology. Patients selected for participation in the study were under treatment regimens that included non-steroidal anti-inflammatory agents. Persons with medical conditions which might affect outcome measures independent from OA pathogenesis or routine treatment for the condition were excluded. The present study met Kuwait University's human subject protection criteria and was approved by the University's Institutional Review Board (IRB)/ethics committee. Informed consent agreements were obtained from all participating subjects.

Each subject was treated topically with 5 ml of the SCE/SCO composition twice daily for 2 months. Treatments were conducted by applying 2.5 ml of the cream to both knees of each participant, followed by dispersal across the kneecap and surrounding skin in a circular motion, continuing until the full 5 ml had been absorbed. Patients in the placebo group were administered 5 ml of a variety of the skin cream created from the seed oil without the flavonoid fraction. The SCE/SCO composition was prepared from seed kernels as previously described.

Treatment Groups and Outcomes Assessed

The participants were randomly assigned into one of 2 treatment groups defined as follows: SCE GROUP: Twenty subjects, administered the SCE/SCO composition twice daily for 2 months; CONTROL (PLACEBO) GROUP: Ten subjects, administered a sour cherry oil-based vehicle without the solid flavonoid fraction (SCE) twice daily for 2 months.

Patients were assessed at baseline and at week 8 of treatment for: (i) Index knee pain using the WOMAC pain subscale (Bellamy et al. 1988); (ii) Serum HO-1; (iii) Serum c-reactive protein (CRP); (iv) Activation of T lymphocytes to express the inflammatory cytokines IL-8, TNF-$\alpha$, IFN-$\gamma$, IL-1$\alpha$, IL-1$\beta$ and IL-6. Blood collection and analysis was conducted according to previously published methods used by this laboratory. Statistical analyses of data were performed using Windows Norusis/SPSS version 17. A p-value of $<0.05$ was considered statistically significant.

Clinical and Laboratory Outcomes

Prior to study enrollment, each patient was screened for compliance with inclusion/exclusion criteria. Parameters evaluated included medical history, current health status (by physical examination), laboratory and radiographic evaluations and a review of current medications. The methodology for measurement of each of these outcomes is summarized below:

(a) Pain Assessment:

Self-assessed pain in the index knee was measured using the 100-mm visual analogue scale (VAS) on the WOMAC pain subscale.

(b) Phlebotomy and Extraction of Peripheral Blood Mononuclear Cells (PBMC):

10-ml samples of sodium heparin-anticoagulated peripheral venous blood were collected from study participants in Vacutainer collection tubes (Becton Dickinson Biosciences Inc., Rutherford, N.J., USA) and diluted 1:1 in sterile phosphate-buffered saline (PBS) followed immediately by isolation of PBMC using density centrifugation on Ficoll-Hypaque gradients (Pharmacia, Uppsala, Sweden); and a Centra-CL-2 centrifuge (MidAtlantic Diagnostics, Inc., Mount Laurel, N.J. 08054 USA).

(c) Cell Culture:

PBMC were separated by Ficoll-paque (Pharmacia, Uppsala, Sweden) density gradient centrifugation. The cells were washed and suspended in RPMI 1640 medium (Gibco BRL, Gaithersburg, Md., USA) at density of $1\times10(6)$ cells/ml. 200 µl cultures in 96-well plates were incubated under humidified conditions for 6 hours at 37° C. in an atmosphere of 5% CO2. PBMC were stimulated in the presence of 50 ng/ml of phorbol 12-myristate 13-acetate (PMA; Sigma, St. Louis, Mo.), 1 ng/ml of ionomycin (Sigma) and 2 mM monensin (Sigma). Here, monensin is added to cells as a glycoprotein export inhibitor, which allows intracellular accumulation of each target cytokine, thus enhancing its signal during flow cytometric analysis.

(d) Flow Cytometric Analysis for Inflammatory Cytokines:

Expression of IL-8, IFN$\gamma$, IL1-$\alpha$, IL1-$\beta$ and IL6 in CD3+CD4+ lymphocytes in freshly collected peripheral blood or for each cell culture stimulation condition was analyzed. Briefly, cells harvested from each culture were first incubated for 15 minutes at room temperature with fluorescein-isothiocyanate (FITC) anti-human CD3+(Dakopatts, A/S, Glostrup, Denmark), then fixed and permeabilized using the Fix and Perm cell permeabilization kit (Life Technologies Inc., Eugene Oreg., U.S.A.). Intracellular labeling of permeablized cells for inflammatory cytokines was accomplished by 30-minute incubations at room temperature, with phycoerythrin (RD1)-conjugated monoclonal antibodies to human IL-8 IFN$\gamma$, IL1-$\alpha$, IL1-$\beta$ and IL6 (BD PharMingen, Heidelberg, Germany). PBMCs were then washed and evaluated by 2-color flow cytometry for expression of each selected cytokine using the FC-500 flow cytometer (Beckman Coulter Corporation, Hialeah, Fla., U.S.A.). Isotypic controls for the antibody used to detect cytokine expression were established for each cell preparation. Positive analysis regions for cells expressing selected CD (cluster of differentiation) immunophenotypic markers and cytokines were set against controls; and specific binding of fluorophore-conjugated antibodies was analyzed according to standard methods recommended by the manufacturer. Lymphocyte subpopulations were identified by position on forward and side scatter plots. Staining of cell surface and internal antigens of interest in preparation for flow cytometry was conducted according to the manufacturer's protocol (InVitrogen Molecular Probes manual: *DETECTION OF INTRACELLULAR ANTIGENS BY FLOW CYTOMETRY* (Rev 03/10) DCC-10-0815 (PN 624923BD). Issue A Initial Issue, 8/03 Rev Issue BD 10/11, Cytomics FC 500 CXP Software IFU Manual, Running Samples Sec 4.1 & Creating Protocols Section 1-19).

(e) ELISA Analysis for HO-1 Expression.

Measurement of lymphocyte expression of HO-1 was made using the StressXpress™ Human HO-1 ELISA Kit (Enzo Life Sciences International, Inc., Plymouth Meeting, Pa., USA). Briefly, lysates made from cells were incubated in 96-well microtiter plates coated with anti-human HO-1 antibody, followed by treatment with secondary/detect antibody and related reagents provided with kits. Cell-associated HO-1 expression was evaluated during the absorbance of the developed kit reagents at 450 nm in a Biotek ELX 808 Microplate Reader. Results are reported as mean values in ng/ml of HO-1 in lymphocyte lysates of each patient group±standard error of the mean (SEM).

(f) ELISA Analysis for c-Reactive Protein (CRP) Levels.

Measurement of CRP was made by using Active US® CRP ELISA Kit (Diagnostic System Laboratories, Inc. Webster, Tex., USA). Briefly, peripheral blood was collected in non-anticoagulated vacutainer tubes (Becton Dickinson Inc.) and allowed to stand at room temperature for 2 hours to form clots, from which serum was extracted with sterile applicators. Serum samples were subsequently incubated in 96-well microtiter plates coated with anti-CRP antibody, followed by treatment with horseradish peroxidase (HRP)-conjugated anti-CRP. CRP concentration in each sample which was proportional to HRP-mediated conversion of a colorimetric substrate was estimated by monitoring of dual wavelength absorbance at 450 and 620 nm using a Synergy HT Multi-Mode Micro plate Reader.

(g) Statistical Analysis.

Wilcoxon signed ranks test was used to compare variables in each group before and after treatment. Correlations between variables within each group were performed using Spearman rank correlation test. The analyses were performed using the SPSS for Windows statistical package version 17 (Norusis/SPSS, Inc.). A P-value of <0.05 was considered statistically significant.

Results

Clinical Outcomes

Figure 2:
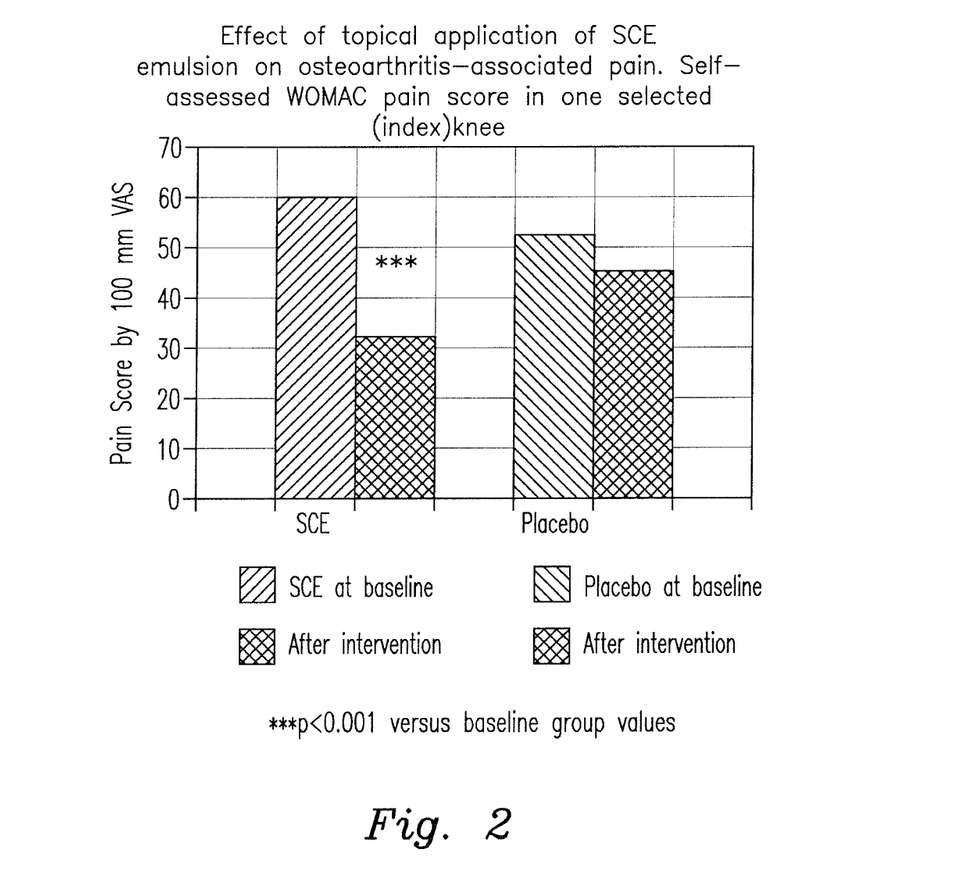
FIG. 2 is a graph showing the effect of topical application of the sour cherry composition on OA-associated pain.

The effect of topical SCE/SCO treatment on joint pain, self-assessed by OA patients in a selected index knee is shown in FIG. 2. When compared to pain scores measured before treatment (baseline values), SCE/SCO-treated patients reported significantly decreased pain following 2 months of daily application of the product ($p<0.001$). In contrast, comparison of pain scores reported by patients in the placebo group at baseline, with scores following 2 months of treatment with the placebo skin cream, revealed only non-significant differences ($p=0.139$).

Figure 3:
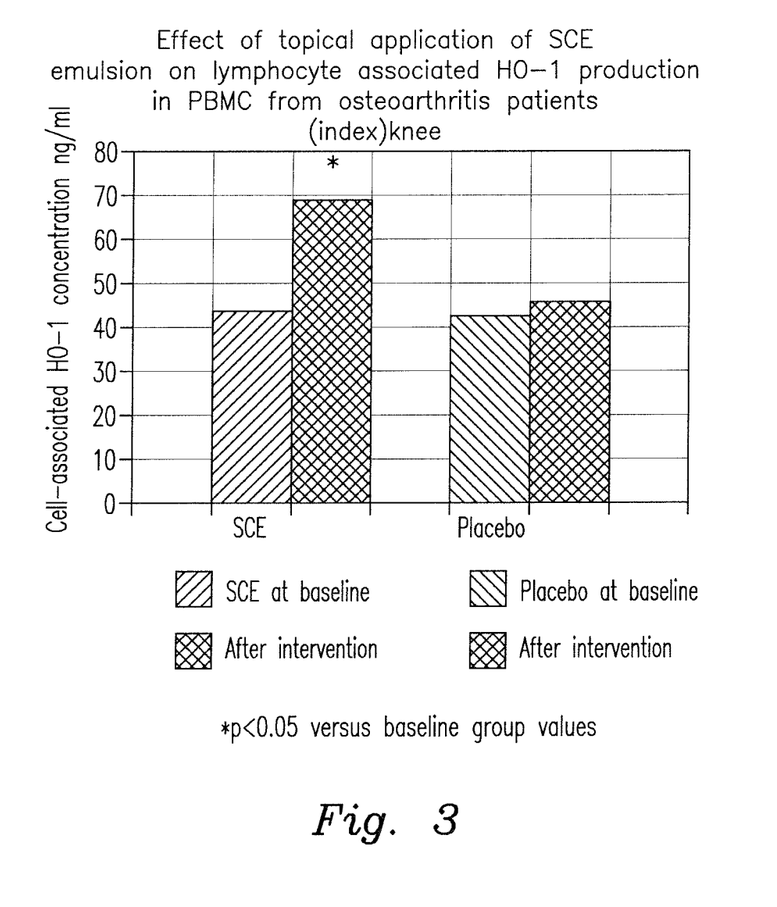
FIG. 3 is a graph showing the effect of topical application of the sour cherry composition on lymphocyte associated HO-1 production in PBMC from OA patients.

FIG. 3 shows expression of leukocyte-associated HO-1 in test and control participants. Measurement of HO-1 content of PBMC lysates taken from both groups reveals significant increases lymphocyte content of the enzyme in cells from SCE/SCO-treated OA patients evaluated by ELISA following 2 months of treatment versus baseline levels ($p<0.05$). A non-significant difference in baseline versus post-treatment PBMC HO-1 levels was revealed for the placebo patients ($p=0.220$).

Figure 4:
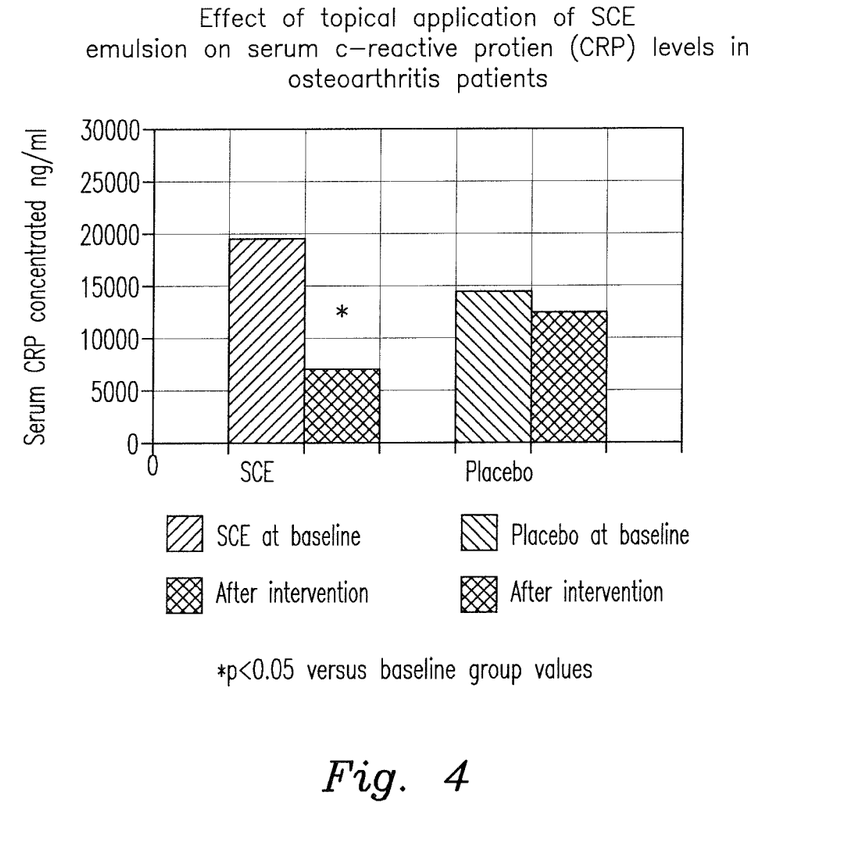
FIG. 4 is a graph showing the effect of topical application of the sour cherry composition on serum c-reactive protein (CRP) levels in OA patients.

Evaluation of c-reactive protein (CRP) in peripheral blood serum of OA patients after 2 months of topical SCE treatment revealed significantly lower levels of this inflammatory biomarker than in samples taken in the same group at baseline ($p<0.005$, FIG. 4). Comparison of serum CRP in placebo-treated subjects showed only non-significant differences between baseline and post-treatment values ($p=0.957$).

Figure 5A:
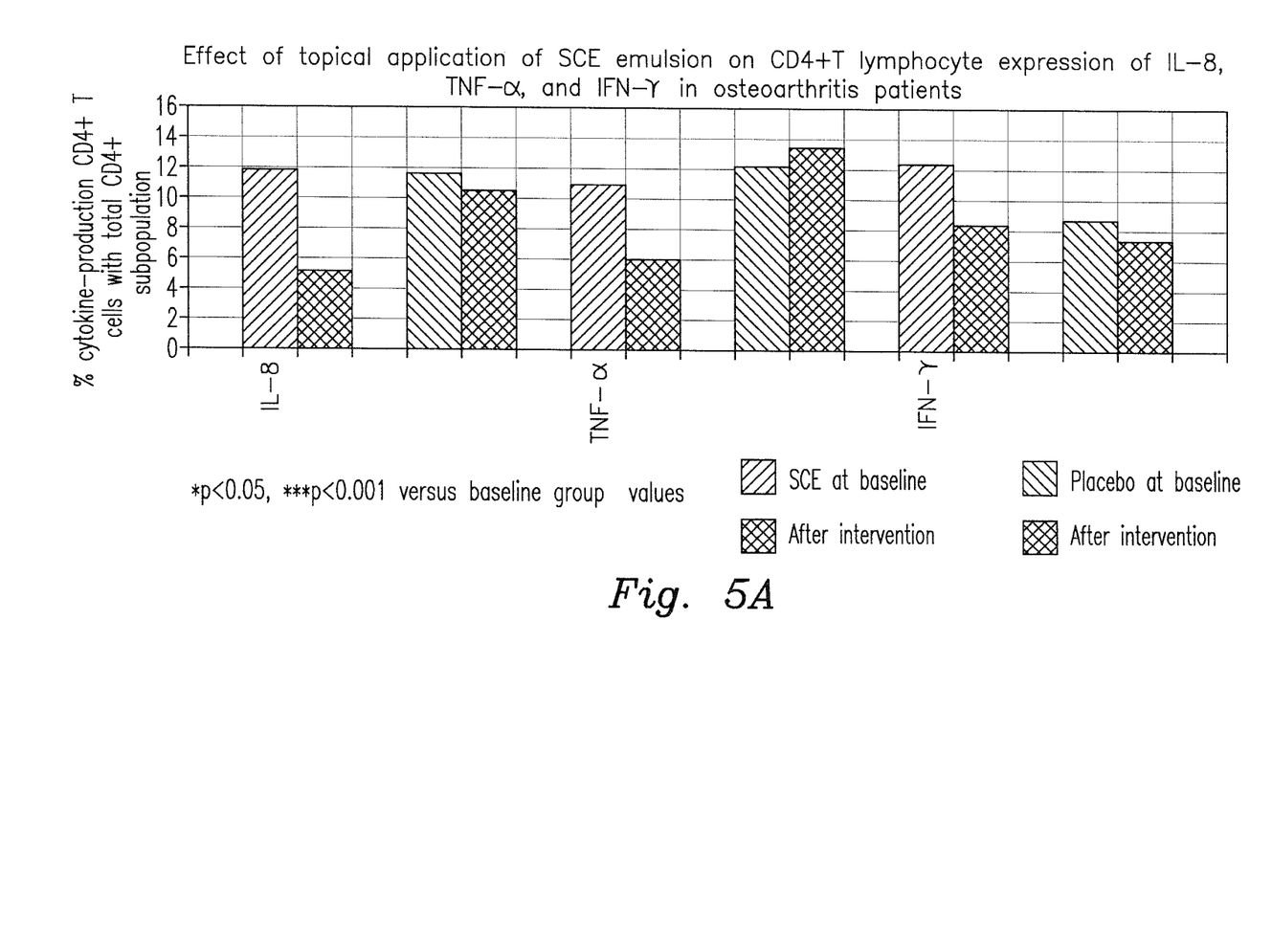
FIG. 5a is a graph showing the effect of topical application of the sour cherry composition on CD 4+T lymphocyte expression of IL-8, TNF-α, and IFN-Y in OA patients.
Figure 5B:
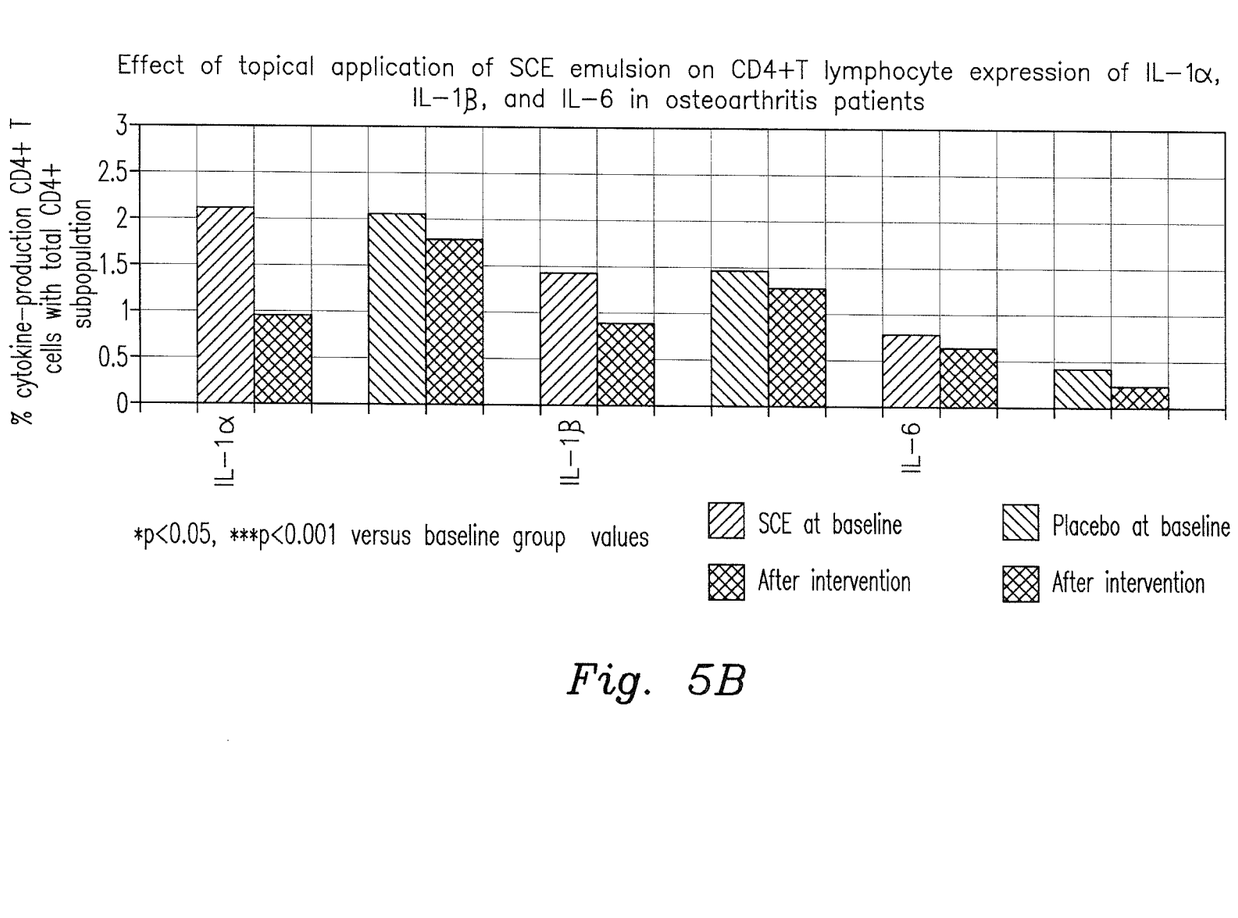
FIG. 5b is a graph showing the effect of topical application of the sour cherry composition on CD 4+T lymphocyte expression of IL-1α, IL-1β, and IL-6 in OA patients.

The effect of SCE/SCO treatment on activation of peripheral blood leukocytes is shown in FIG. 5. Here, the effect of treatments on CD4+ T cells is shown, since these cells are a major source of inflammatory the cytokines contributing to OA pathogenesis. It is nevertheless anticipated that SCE/SCO also alters pro-inflammatory signaling by macrophages and other tissue. Ongoing studies are evaluating the scope of SCE/SCO-mediated effects in other cell types. Relative to baseline measurements, PBMC from SCE/SCO-treated OA patients cultured with PMA/I, contained significantly lower post-treatment representation of CD4+IL-8+($p<0.001$), CD4+TNF-$\alpha$+($p<0.005$) and CD4+IFN-$\gamma$+($p<0.005$) (5A), CD4+IL-1$\alpha$+($p<0.005$) and CD4+IL-1$\beta$+($p<0.005$), but not CD4+IL-6 ($p=0.494$) (5B). In these experiments, comparison of cells from blood of OA patients taken at baseline, versus placebo-treated patients show non-significant differences in representation of CD4+ T cells activated to express IL-8 ($p=0.730$), TNF-$\alpha$ ($p=0.165$) and IFN-$\gamma$ ($p=0.160$) (5A), IL-1$\alpha$ ($p=0.620$), IL-1$\beta$ ($p=0.406$) and IL-6 ($p=0.240$) (5B).

Implication of Preliminary Human Trials

The representative investigation described above was a double-blind clinical trial, evaluating a hypothesis that the SCE/SCO composition as set forth, administered topically, reduces joint pain and systemically inhibits expression of inflammatory cytokines that promote OA pathogenesis; along with reduction in c-reactive protein (CRP), and numbers of T cells activated to express IL-8, TNF-$\alpha$, IFN-$\gamma$, IL-1$\alpha$, and IL-1$\beta$. These results were obtained by persons administered extracts of the sour cherry seed kernel comprising both solid sour cherry seed extract (SCE) and solid cherry seed oil (SCO), but not the fruit itself.

Based on previous investigations and the significantly increased lymphocyte HO-1 expression noted in SCE-treated patients relative to baseline and placebo (FIG. 3) the therapeutic mechanisms likely include HO-1-mediated quenching of proinflammatory reactive oxygen species. In this study, we observed that topical treatment of OA patients with a SCE/SCO preparation of sour cherry flavonoids that include HO-1 inducers which therapeutically diminish oxidative stress burden on tissue significantly abated major OA symptoms. These effects occurred via inhibition of CD3+ T cell expression of inflammatory cytokines, thus demonstrating the capacity of this plant material to ameliorate OA severity by altering a major underlying contributor to disease progression.

Relevance of HO-1 Increases in SCE/SCO-Treated Subjects:

In the representative human study described above, the significantly increased expression of HO-1 by PBMC, isolated from the blood of SCE-treated subjects (p<0.05) shown in FIG. 3, is consistent with the expected effect of transdermal delivery of HO-1-inducers at levels sufficient to mediate systemic up-regulation of the enzyme. Indeed, increased activity of HO-1 in immune cells (and possibly other tissue) may account for the significant SCE treatment-associated reduction in serum CRP shown in FIG. 4 (p<0.05), as CRP level is a well-known correlate of the severity of inflammatory diseases, including OA. These observations further underscore the role of disease- or trauma-related HO-1 expression as a general adaptive response to dysregulated inflammation with therapeutic potential in many clinical venues. It is therefore tempting to speculate that SCE/SCO-induced increases in HO-1 expression is the critical mediator of significant treatment-related decreases in the representation of CD3+ subpopulations activated to express the inflammatory cytokines IL-8, TNF-α, IFN-γ, IL-1α, IL-1β, and IL-6 (p<0.05), shown in FIGS. 5$a$ and 5$b$.

It is understood that equivalents and substitutions for certain elements and steps set forth above may be obvious to one of ordinary skill in the art, and therefore the true scope and definition of the invention is to be as set forth in the following claims. The examples and any preferred embodiments as set forth above are meant to be non-limiting as to the scope of the invention.

We claim:

1. A method of producing a biotherapeutic anti-inflammatory composition comprising the steps of:
    (a) providing a lipophilic component comprising at least some ingredients not present naturally in sour cherry seeds;
    (b) providing a hydrophilic component comprising at least some ingredients not present naturally in sour cherry seeds;
    (c) providing solid flavonoid-rich sour cherry seed extract in powdered form;
    (d) providing sour cherry seed oil;
    (e) heating said lipophilic component to a sufficient temperature to melt or liquefy said lipophilic component and separately heating said hydrophilic component to a sufficient temperature to melt or liquefy said hydrophilic component;
    (f) mixing said melted or liquefied lipophilic component and said melted or liquefied hydrophilic component;
    (g) allowing said mixed heated lipophilic and hydrophilic components to cool to form a cream base; and
    (h) mixing said sour cherry seed oil and said solid flavonoid-rich sour cherry seed extract in powdered form into said cream base.

2. The method of claim 1, wherein said step of mixing said sour cherry seed oil and said solid flavonoid-rich sour cherry seed extract in powdered form into said cream base comprises mixing an amount of said sour cherry seed oil and an amount of said solid flavonoid-rich sour cherry seed extract in powdered form, wherein such that said sour cherry seed oil is approximately 3-5 wt % of said composition and said solid flavonoid-rich sour cherry seed extract in powdered form is approximately 3-5 wt % of said composition.

3. The method of claim 1, wherein said step of providing a lipophilic component comprises the step of mixing lanolin, cetylic and stearylic alcohol, stearin, and isopropyl myristate; and
    wherein said step of providing a hydrophobic component comprises the step of mixing vitamin C, sodium lauryl sulphate, glycerin, propylene glycol and water.

4. The method of claim 3, wherein said step of providing a lipophilic component comprises the step of mixing approximately 20 wt % lanolin, approximately 20 wt % cetylic and stearylic acid, approximately 40 wt % stearin, and approximately 20 wt % isopropyl myristate to form said lipophilic component; and
    wherein said step of providing a hydrophilic component comprises the step of mixing approximately 1.2 wt % vitamin C, approximately 3.1 wt % sodium lauryl sulphate, approximately 7.7 wt % glycerin, approximately 7.7 wt % propylene glycol, and approximately 80.3 wt % water to form said hydrophilic component.

5. The method of claim 3, wherein said steps of providing a lipophilic component, providing a hydrophobic component, providing solid flavonoid-rich sour cherry seed extract in powdered form, and providing sour cherry seed oil comprise providing approximately 5 wt % lanolin, approximately 5 wt % cetylic and stearylic alcohol, approximately 10 wt % stearin, approximately 5 wt % isopropyl myristate, approximately 0.8 wt % vitamin C, approximately 2 wt % sodium lauryl sulphate, approximately 5 wt % glycerin, approximately 5 wt % propylene glycol, approximately 52.2 wt % water, approximately 5 wt % solid flavonoid-rich sour cherry seed extract, and approximately 5 wt % sour cherry seed oil relative to said composition.

6. The method of claim 1, wherein said step of heating said lipophilic component and separately heating said hydrophilic component comprises heating each component in a water bath at a temperature of approximately 50-60° C.

7. A method of producing a biotherapeutic anti-inflammatory topical composition in the form of a phase-stable emulsion, said composition comprising a mixture of solid flavonoid-rich sour cherry seed extract in powdered fan I previously separated from sour cherry seeds and sour cherry seed oil previously separated from sour cherry seeds, wherein said solid flavonoid-rich sour cherry seed extract in powdered form and said sour cherry seed oil are present in amounts producing an anti-inflammatory effect, said composition altering the underlying pathomechanisms caused by dysregulated inflammatory processes by inhibiting production of disease-associated inflammatory cytokines by CD3+T lymphocytes, inhibiting the inflammation-associated serum biomarker c-reactive protein, and increasing expression of heme oxygenase-1 by peripheral blood leukocytes, when topically applied, comprising the steps of:
    (a) providing a lipophilic component comprising at least some ingredients not present naturally in sour cherry seeds;
    (b) providing a hydrophilic component comprising at least some ingredients not present naturally in sour cherry seeds;
    (c) providing solid flavonoid-rich sour cherry seed extract in powdered form;
    (d) providing sour cherry seed oil;
    (e) heating said lipophilic component to a sufficient temperature to melt or liquefy said lipophilic component and separately heating said hydrophilic component to a sufficient temperature to melt or liquefy said hydrophilic component;
    (f) mixing said melted or liquefied lipophilic component and said melted or liquefied hydrophilic component;
    (g) allowing said mixed heated lipophilic and hydrophilic components to cool to form a cream base; and
    (h) mixing said sour cherry seed oil and said solid flavonoid-rich sour cherry seed extract in powdered form into said cream base.

8. The method of claim 7, wherein said step of mixing said sour cherry seed oil and said solid flavonoid-rich sour cherry seed extract in powdered form into said cream base comprises mixing an amount of said sour cherry seed oil and an amount of said solid flavonoid-rich sour cherry seed extract in powdered form, wherein said sour cherry seed oil is approximately 3-5 wt % of said composition and said solid flavonoid-rich sour cherry seed extract in powdered form is approximately 3-5 wt % of said composition.

9. The method of claim 7, wherein said step of providing a lipophilic component comprises the step of mixing lanolin, cetylic and stearylic alcohol, stearin, and isopropyl myristate; and wherein said step of providing a hydrophobic component comprises the step of mixing vitamin C, sodium lauryl sulphate, glycerin, propylene glycol, and water.

10. The method of claim 9, wherein said step of providing a lipophilic component comprises the step of mixing approximately 20 wt % lanolin, approximately 20 wt % cetylic and stearylic acid, approximately 40 wt % stearin, and approximately 20 wt % isopropyl myristate to form said lipophilic component; and wherein said step of providing a hydrophilic component comprises the step of mixing approximately 1.2 wt % vitamin C, approximately 3.1 wt % sodium lauryl sulphate, approximately 7.7 wt % glycerin, approximately 7.7 wt % propylene glycol, and approximately 80.3 wt % water to form said hydrophilic component.

11. The method of claim 9, wherein said steps of providing a lipophilic component, providing a hydrophobic component, providing solid flavonoid-rich sour cherry seed extract in powdered form, and providing sour cherry seed oil comprise providing approximately 5 wt % lanolin, approximately 5 wt % cetylic and stearylic alcohol, approximately 10 wt % stearin, approximately 5 wt % isopropyl myristate, approximately 0.8 wt % vitamin C, approximately 2 wt % sodium lauryl sulphate, approximately 5 wt % glycerin, approximately 5 wt % propylene glycol, approximately 52.2 wt % water, approximately 5 wt % solid flavonoid-rich sour cherry seed extract, and approximately 5 wt % sour cherry seed oil relative to said composition.

12. The method of claim 1, wherein said step of heating said lipophilic component and separately heating said hydrophilic component comprises heating each component in a water bath at a temperature of approximately 50-60° C.

* * * * *